(12) United States Patent
Goetz et al.

(10) Patent No.: US 8,015,978 B2
(45) Date of Patent: Sep. 13, 2011

(54) LOCATING AN IMPLANTED OBJECT BASED ON EXTERNAL ANTENNA LOADING

(75) Inventors: Steven M. Goetz, North Oaks, MN (US); Todd V. Smith, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/976,297

(22) Filed: Dec. 22, 2010

(65) Prior Publication Data

US 2011/0118591 A1    May 19, 2011

Related U.S. Application Data

(62) Division of application No. 11/186,388, filed on Jul. 20, 2005, now Pat. No. 7,878,207.

(60) Provisional application No. 60/589,538, filed on Jul. 20, 2004.

(51) Int. Cl.
*A61B 19/00* (2006.01)
*A61B 5/00* (2006.01)

(52) U.S. Cl. ...................................... 128/899

(58) Field of Classification Search .......... 128/897–899; 340/10.1, 551; 342/250, 385; 600/9–15, 600/424; 324/67, 207.15, 207.16, 228, 232, 324/239, 328, 329
See application file for complete search history.

(56) References Cited

U.S. PATENT DOCUMENTS

| | | | |
|---|---|---|---|
| 4,223,679 A | 9/1980 | Schulman et al. | |
| 4,255,710 A | 3/1981 | Weber | |
| 4,281,664 A | 8/1981 | Duggan | |
| 4,361,153 A | 11/1982 | Slocum et al. | |
| 4,494,545 A | 1/1985 | Slocum et al. | |
| 4,541,431 A | 9/1985 | Ibrahim et al. | |
| 4,642,786 A * | 2/1987 | Hansen ........................ | 702/153 |
| 5,057,095 A | 10/1991 | Fabian | |
| 5,117,825 A | 6/1992 | Grevious | |

(Continued)

FOREIGN PATENT DOCUMENTS

EP    0 300 552 A1    1/1989
(Continued)

OTHER PUBLICATIONS

Notification of Transmittal of the International Search Report and the Written Opinion dated Jan. 18, 2006, International Application No. PCT/US2005/025895, (15 pages).

(Continued)

*Primary Examiner* — Charles A Marmor, II
*Assistant Examiner* — Catherine E Burk
(74) *Attorney, Agent, or Firm* — Shumaker & Sieffert, P.A.

(57) ABSTRACT

In general, the invention is directed to techniques for locating an implanted object using an external antenna. The implanted object may be, for example, an internal antenna that facilitates recharging of and/or communication with an implantable medical device. An external device coupled to the external antenna drives the antenna with a plurality of waveforms. Asymmetry in the loading profile of the external antenna when it is driven by the plurality of waveforms allows the external device or another device to determine the location of the implanted object relative to the external antenna. The external device or other device may provide information to a user based on the determined location of the implanted object relative to the external antenna, such as information to help a user position the external antenna with respect to an internal antenna in embodiments in which the implanted object is an internal antenna.

12 Claims, 8 Drawing Sheets

U.S. PATENT DOCUMENTS

| | | | |
|---|---|---|---|
| 5,314,453 | A | 5/1994 | Jeutter |
| 5,324,315 | A | 6/1994 | Grevious |
| 5,562,714 | A | 10/1996 | Grevious |
| 5,690,693 | A | 11/1997 | Wang et al. |
| 5,702,431 | A | 12/1997 | Wang et al. |
| 5,766,232 | A | 6/1998 | Grevious et al. |
| 6,009,878 | A | 1/2000 | Weijand et al. |
| 6,088,619 | A | 7/2000 | Hein et al. |
| 6,212,430 | B1 | 4/2001 | Kung |
| 6,305,381 | B1 | 10/2001 | Weijand et al. |
| 6,321,118 | B1 | 11/2001 | Hahn |
| 6,473,652 | B1 | 10/2002 | Sarwal et al. |
| 6,516,227 | B1 | 2/2003 | Meadows et al. |
| 6,647,299 | B2 | 11/2003 | Bourget |
| 7,248,165 | B2 | 7/2007 | Collins et al. |
| 2001/0000187 | A1 | 4/2001 | Peckham et al. |
| 2002/0151770 | A1 | 10/2002 | Noll, III et al. |
| 2003/0114899 | A1 | 6/2003 | Woods et al. |
| 2003/0120323 | A1 | 6/2003 | Meadows et al. |
| 2004/0113790 | A1 | 6/2004 | Hamel et al. |
| 2005/0075697 | A1 | 4/2005 | Olson et al. |

FOREIGN PATENT DOCUMENTS

| | | |
|---|---|---|
| WO | WO 87/04801 | 8/1987 |
| WO | WO 96/40367 | 12/1996 |
| WO | WO 99/38438 | 8/1999 |

OTHER PUBLICATIONS

Notification of Transmittal of the International Preliminary Report on Patentability dated Oct. 30, 2006, International Application No. PCT/US2005/025895, (13 pages).

Reply to Written Opinion dated May 19, 2006, International Application No. PCT/US2005/025895, (19 pages).

* cited by examiner

LOCATING AN IMPLANTED OBJECT BASED ON EXTERNAL ANTENNA LOADING

This application is a divisional of application Ser. No. 11/186,388, filed Jul. 20, 2005, which claims the benefit of U.S. Provisional Application No. 60/589,538, filed Jul. 20, 2004, the entire contents of both of which are incorporated herein by reference in their entirety.

TECHNICAL FIELD

The invention relates to techniques for aligning an external object, such as a primary antenna, with an implanted object, such as a secondary antenna.

BACKGROUND

Many implantable medical device systems use magnetically coupled antennas for one or both of telemetry communications and inductive recharging of a power source of the implantable medical device. In both scenarios, the relative positioning of the primary and secondary, i.e., external and internal, antennas is important to the performance of the system. This is especially true for recharging, where the positioning of the primary antenna has a dramatic impact on the efficiency of the recharge procedure and on the associated time that must be spent recharging. Localization of an external device relative to an implanted object can also be very important in, for example, implantable drug pump systems, where it may be necessary to locate a subcutaneous refill port.

Some existing implantable medical device systems incorporate an antenna, or other implanted object, locating feature. This feature has variously been implemented using a signal strength approach, e.g., measuring the strength of a telemetry signal sent by an implantable medical device to the external antenna, or by using a metal detection approach, e.g., measuring the loading of the external antenna caused by the proximity of the implant. However, both of these techniques are limited to providing an output proportional to the distance of separation. This output, while somewhat useful in guiding the user into better placement, does not contain enough information to generate precise guidance.

Systems have also been built that locate an implanted object using multiple external antennas to triangulate the position of implanted object, e.g., an internal antenna. This type of system can provide more detailed guidance to a user for location, but only at the expense of additional external hardware, and additional consumption of power to drive the additional antennas.

SUMMARY

In general, the invention is directed to techniques for locating an implanted object using an external antenna. The implanted object may be, for example, an internal antenna that facilitates recharging of and/or communication with an implantable medical device (IMD), a refill port for a reservoir of an IMD that includes a pump, i.e., an implantable pump, or an IMD itself. When the external antenna is driven with a waveform, induced currents in the implanted object cause loading at the external antenna. Asymmetry in the loading profile of the external antenna when it is driven by different waveforms, e.g., waveforms with different amplitudes, frequencies, pulse widths, or shapes, allows the location of the implanted object relative to the external antenna to be determined.

A system according to the invention may include an external device coupled to the external antenna. The external device may be, for example, an external programming or recharging device for an IMD with which the implanted object is associated. When the user initiates an implanted object location operation, or another operation for which location of an implanted object is desired, such as recharging, telemetry communication, or refilling, the external device may begin driving the external antenna with two or more waveforms in succession. For each of the waveforms, the external device measures the value of an electrical parameter associated with the antenna, such as a current through the external antenna or a voltage across the antenna, when the antenna is driven with the waveform. The external device, or another device, determines the location of the implanted object relative to the external antenna based on the measured electrical parameter values for each of the waveforms.

The measured electrical parameter values differ and, due the asymmetric loading profile of the external antenna, the difference between the measured electrical parameter values varies as a function of the location of the external antenna relative to the implanted object. The external device or other device may apply a plurality of equations to the measured values of the electrical parameter, each of the equations defining a position variable as a function of the electrical parameter. The position variables defined by the equations may include radial distance, depth, or angle, and values thereof determined based on the measured electrical parameter values may indicate the location of the implanted object relative to the external antenna.

The external device or other device may provide information to a user indicating the determined location of the implanted object relative to the external antenna. The information may include, for example, an arrow that points in the direction of the implanted object relative to the external antenna, superimposed images (such as circles) that will be lined up when the external antenna is aligned with the implanted object, or a text or audio description of the location of the implanted object relative to the external antenna. In some embodiments, such as information may be provided to a user as instructions, such as instructions to help a user position the external antenna with respect to an internal antenna in embodiments in which the implanted object is an internal antenna.

The one or more equations that may be used to determine the position of the internal object relative to the external antenna in the manner described above may be determined prior to use of the external device and antenna to locate the implanted object, e.g., prior to implantation of the object, when the location of the device is known. In particular, the external device may drive the external antenna with the two or more waveforms that will be later used during location of the object, while the external antenna is moved through a three-dimensional region proximate to the object. For each of the driving waveforms, the external device periodically measures value of the electrical parameter when the external antenna is moved through the region.

For each of the waveforms, the external device may determine a relationship between the position of the external antenna (x,y,z) relative to the internal object and the electrical parameter, based on the measured values of the electrical parameter and the locations of the antenna when the values were measured. From these position/electrical parameter relationships, the external device may calculate equations, such as parametric equations of the form $ep = a + b*z + c*z^2 + d*r$, where ep is the electrical parameter, e.g., current through the antenna or voltage across the antenna, z is the depth, r is the radial distance, and a, b, c and d are coefficients calculated using known z and r values. The values of r (radial distance) may be recorded as the antenna is moved through the three-dimensional space, or calculated afterwards based on recorded x and y values. The external device may solve the equations for each of the position variables as a function of the electrical parameter. For example, the external device may solve the parametric equations for r and z in terms of the electrical parameter. In this manner, the external device may determine the plurality of equations, each equation relating a respective position variable to the electrical parameter In some embodiments, one or more other devices, rather than the external device later used to locate the implanted object, perform some or all of the functions associated with determination of the equations. For example, a robotic platform driver may move the external antenna through the three-dimensional region, and periodically determine the position of the antenna relative to the known position of the implantable object. In such embodiments, the platform driver or another computing device may determine the equations based on electrical parameter values received from the external device, and program the external device with the equations. A different external device may be used to drive the antenna and measure electrical parameter values during equation determination, and the external device that will later be used to locate the implanted object may be programmed with determined equations and the waveforms.

Further, another device may perform some of the functions associated with the eventual location of the implanted object. For example, a separate computing device may receive measured electrical parameter values from the external device and apply the equations to the measured values to determine the location of the implanted object relative to the antenna. The other device may also provide information to a user based on the determined location, in the manner described above.

In one embodiment, the invention is directed to a method comprising driving an external antenna with a first waveform, measuring a first value of an electrical parameter associated with the external antenna while the external antenna is driven with the first waveform, driving the external antenna with a second waveform, measuring a second current value of the electrical parameter while the external antenna is driven with the second waveform, and determining a location of an implanted object relative to the external antenna based on the first and second electrical parameter values.

In another embodiment, the invention is directed to a system comprising an external antenna, an external device coupled to the external antenna, and a processor. The external device drives the external antenna with a first waveform, measures a first an electrical parameter associated with the external antenna while driving the external antenna with the first waveform, drives the external antenna with a second waveform, and measures a second value of the electrical parameter while driving the external antenna with the second waveform. The processor determines a location of an implanted object relative to the external antenna based on the first and second electrical parameter values.

In another embodiment, the invention is directed to a computer-readable medium comprising instructions. The instructions cause a programmable processor to control generation of a first waveform to drive an external antenna, measure a an electrical parameter associated with the external antenna while the external antenna is driven with the first waveform, control generation of a second waveform to drive the external antenna, measure a second value of the electrical parameter while the external antenna is driven with the second waveform, and determine a location of an implanted object relative to the external antenna based on the first and second electrical parameter values.

In another embodiment, the invention is directed to a system comprising an external antenna, an external device coupled to the external antenna, and a processor. The external device drives the external antenna with the first waveform while the external antenna is moved through a three-dimensional region proximate to an implantable object a first time, periodically measures values of an electrical parameter associated with the external antenna while the external antenna is moved through the three-dimensional region the first time and driven with the first waveform, drives the external antenna with a second waveform while the external antenna is moved through the three-dimensional region a second time, and periodically measures values of the electrical parameter while the external antenna is moved through the three-dimensional region the second time and driven with the second waveform. The processor determines a first position/electrical parameter relationship based on the electrical parameter values measured while the external antenna was driven with the first waveform and positions within the three-dimensional region at which the external antenna was located when the electrical parameter values were measured, determines a second position/electrical parameter relationship based on the electrical parameter values measured while the external antenna was driven with the second waveform and positions within the three-dimensional region at which the external antenna was located when the electrical parameter values were measured, and determines first and second equations based on the first and second position/current relationships. The first equation defines a first position variable as a function of the electrical parameter, and the second equation defines a second position variable as a function of the electrical parameter.

In another embodiment, the invention is directed to a computer-readable medium comprising instructions. The instructions cause a programmable processor to control generation of a first waveform to drive an external antenna while the external antenna is moved through a three-dimensional region proximate to an implantable object a first time, periodically measure values of an electrical parameter associated with the external antenna while the external antenna is moved through the three-dimensional region the first time and driven with the first waveform, determine a first position/electrical parameter relationship based on the electrical parameter values measured while the external antenna was driven with the first waveform and positions within the three-dimensional region at which the external antenna was located when the electrical parameter values were measured, control generation of a second waveform to drive the external antenna while the external antenna is moved through the three-dimensional region a second time, periodically measure values of the electrical parameter while the external antenna is moved through the three-dimensional region the second time and driven with the second waveform, determine a second position/electrical parameter relationship based on the electrical parameter values measured while the external antenna was driven with the second waveform and positions within the three-dimensional region at which the external antenna was located when the electrical parameter values were measured, and determine first and second equations based on the first and second position/electrical parameter relationships. The first equation defines a first position variable as a function of the electrical parameter, and the second equation defines a second position variable as a function of the electrical parameter.

The invention may be capable of providing one or more advantages. For example, systems that utilize implanted object location techniques according to the invention may be able provide a user with more detailed information regarding the location of the object relative to the external antenna than is provided by systems using conventional implanted object location techniques. Such information may allow the user to more quickly and accurately locate the object than is possible with conventional systems.

In embodiments in which the implanted object is an internal antenna, for example, more accurate placement of the external antenna relative to the internal antenna may improve signal strength for telemetry communications or coupling efficiency for recharging an IMD power source. Improved coupling efficiency for recharging may allow shorter recharge cycles. As another example, more accurate location of a refill port of an implantable pump may allow more accurate refilling of the implantable pump, e.g., with fewer needle sticks.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
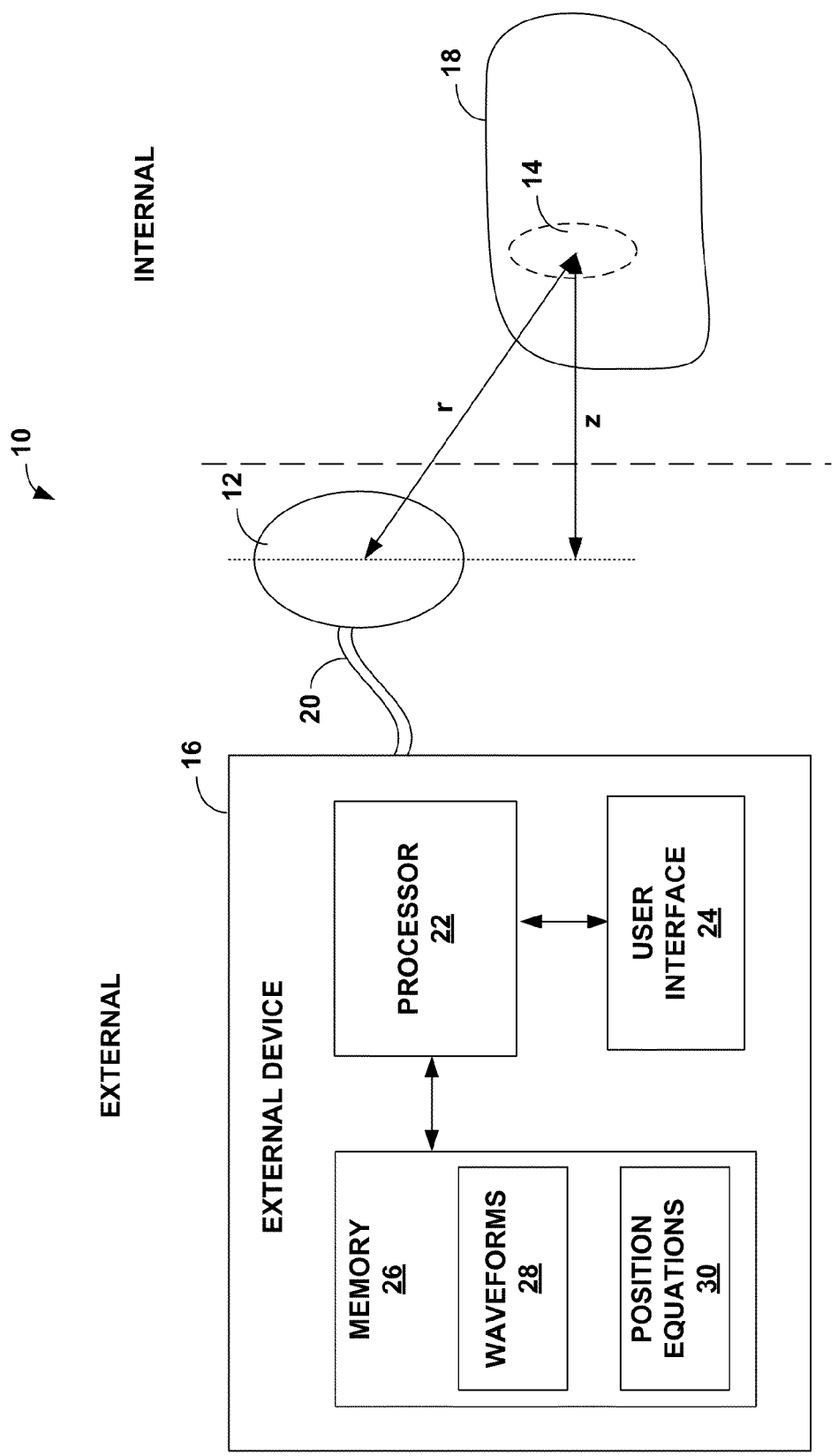
FIG. 1 is a block diagram illustrating an example system for location of an implanted object.

FIG. 1 is a block diagram illustrating an example system 10 for location of an implanted object. System 10 includes an external antenna 12 used to locate an implanted object 14, and an external device 16 coupled to the external antenna 12 by a cable or other connector 20. External antenna 12 may be, for example, a coil antenna.

In the illustrated embodiment, implanted object 14 is an internal, e.g., secondary, antenna, which may also be a coil antenna, associated with an implantable medical device (IMD) 18. In such embodiments, internal antenna 14 may be used with external, e.g., primary, antenna 12 for telemetry communication between external device 16 and IMD 18, or for recharging of a power source of IMD 18. In such embodiments, identification of the location of internal antenna 14 relative to external antenna 12 may increase the accuracy of placement of external antenna 12, e.g., alignment of antennas 12, 14, which may improve signal strength for telemetry communications, or coupling efficiency during recharging.

In such embodiments, external device 16 may be a recharging device, programming device, or other interrogation device. Internal antenna 14 may, as illustrated in FIG. 1, be located within a housing of IMD 18. However, internal antenna 14 may be located on the outside of the housing of IMD 18, or be a separate structure located some distance away from the housing of IMD 18 and coupled to IMD 18, e.g., via a cable.

The invention is not limited to embodiments in which implanted object 14 comprises an internal antenna. For example, implanted object 14 may be a fill port associated with an IMD 18 that comprises an implantable reservoir pump. In such embodiments, accurate location of a refill port may allow more accurate refilling of the reservoir, e.g., with fewer needle sticks. As another example, an implanted object 14 may be an IMD itself. Further, external device 16 need not be a recharging or programming device, but may be any external device, and used whenever location of an implanted object is desired. IMD 18 may be an implantable neurostimulator, muscle stimulator, gastric stimulator, pelvic nerve stimulator, bladder stimulator, cardiac pacemaker, pacemaker device with cardioversion and/or defibrillation capabilities, pump, or other implantable device.

In general, external device 16 exploits asymmetry in the loading profile of external antenna 12 when it is driven by a plurality of different waveforms to determine the location of implanted object 14 relative to external antenna 12. When antenna 12 is driven with a waveform, current flows through external antenna 12, thereby generating a magnetic field. When a conductive object, such as the housing of IMD 18 or implanted antenna 14, is placed in close proximity to the coil of external antenna 12, the magnetic field causes currents to flow in the conductive object. These currents in turn generate their own magnetic fields that resist the action of the field generated by external antenna 12, which in turn affects electrical parameters associated with the external antenna, e.g., current through or voltage across the external antenna. Thus, the values of such electrical parameters are related to the amount of conductive material within the vicinity of the magnetic field of external antenna.

When antenna 12 is driven with varying waveforms, such as waveforms with different amplitudes, pulse widths, shapes and/or frequencies, the values of the electrical parameter will differ from waveform to waveform. Due the asymmetric loading profile of external antenna 12, the difference between the measured electrical parameter values also varies as a function of the location of the external antenna relative to the implanted object. The varying difference between the measured electrical parameter values for each of a plurality of different waveforms used to drive antenna 12 may thus be used to determine the location of an implanted object relative to external antenna 12.

When the user initiates an antenna finding operation (or an operation for which antenna location is critical, such as recharging), such as by providing an input via a user interface 24 of external device 16, a processor 22 of external device 16 controls measurement at two or more measurement conditions in succession. For example, processor 22 may control generation of a first waveform to drive external antenna 12, and measure a first value of an electrical parameter associated with the antenna, e.g., current through or voltage across the antenna, while the antenna is driven with the first waveform. Processor 22 may then control generation of a second waveform, different from the first, to drive external antenna 12, and measure a second value of the electrical parameter while the antenna is driven with the second waveform. Although not shown in the Figures, external device 16 may include circuitry, such as oscillators and amplifiers, controlled by processor 22 for generation of different waveforms. External device 16 may also include circuitry known in the art for measuring electrical parameter values within a circuit, such as resistors and capacitors, which processor 22 may use to determine the electrical parameter values.

Processor 22 determines a location of internal antenna 14 relative to external antenna 12 based on the first and second values of the electrical parameter. In some embodiments, processor 22 applies position equations to the measured electrical parameter values to determine the location of internal antenna 14 relative to external antenna 12. Each of the position equations defines a position variable in terms of the electrical parameter. As examples, the following example position equations [1] and [2] define radial distance (r) and depth (z), respectively, as a function of current through the external antenna when driven with two different waveforms:

$$r = \frac{(i_{(1)} - a - b*z - c*z^2)}{d} \quad [1]$$

$$z = \frac{(-B \pm \sqrt{B^2 - 4*A*C})}{2*A} \quad [2]$$

In the equations [1] and [2] above, r is the radial distance, and z is the depth. Further:

$$A = v - \frac{w*c}{d} \quad [3]$$

$$B = u - \frac{w*b}{d} \quad [4]$$

$$C = t - \frac{w*a}{d} + \frac{w*i_{(1)}}{d} - i_{(2)} \quad [5]$$

Values $i_{(1)}$ and $i_{(2)}$ are the currents measured when the external antenna was driven with the first and second waveforms respectively, and a, b, c, d, t, u, v and w are coefficients calculated using known depths (z) and radial distances (r). Applying equations [1] and [2] to current values measured when external antenna 12 was driven with first and second waveforms, processor 22 may determine a radial distance between antennas 12, 14 and a depth of internal antenna 14 relative to external antenna 12.

In other embodiments, the equations may define other position variables in terms of an electrical parameter. For example, in other embodiments, processor 22 may apply equations that define radial distance and angle, instead of radial distance and depth. As shown in FIG. 1, a memory 26 of external device 16 may store information describing the waveforms 28 with which antenna 12 is to be driven, and the position equations 30.

Based on the determined location of internal antenna 14, processor 22 may provide location information to a user to help the user locate the internal antenna, e.g., align the external and internal antennas, via user interface 24. For example, processor 22 may display an arrow that points in the direction the user should move external antenna 12, superimposed images (such as circles) that must be aligned, a text description of where to move external antenna 12, or an audible description, via user interface 24. For example, a text description may be output to the user identifying a radial distance from the implantable medical device. User interface 24 may include a display, a speaker, a Light Emitting Diode (LED), or the like, and may also include any of a variety of input media, such as buttons, switches, a keypad, a touch screen, or a pointing device.

Although the antenna positioning techniques are described in terms of applying two different drive waveforms, additional drive waveforms may be used to obtain more detailed positioning. For example, addition of a third drive waveform will allow processor 22 to apply equations that define radial distance (r) and angle (θ), rather than depth, in terms of an electrical parameter. The angle (θ) may provide greater information regarding the direction in which the internal antenna is located relative to the external antenna than is known when depth (z) is determined.

Furthermore, the techniques of the invention can be integrated with telemetry strength techniques for estimating distance. In particular, processor 22 may initiate telemetry communication with IMD 18 via antennas 12, 14 to confirm the presence of IMD 18 and/or internal antenna 14.

Moreover, external antenna 12, internal antenna 14 or another implanted object, or IMD 18 may be specifically designed to exaggerate the asymmetric loading of external antenna 12. For instance, external antenna 12, internal antenna 14, or the housing of the implantable medical device 18 may be an oblong shape instead of a circular shape.

Processor 22 may include a microprocessor, a controller, a digital signal processor (DSP), an application specific integrated circuit (ASIC), a field-programmable gate array (FPGA), discrete logic circuitry, or the like. Memory 26 may include program instructions that, when executed by processor 22, cause processor 22 and external device 15 to perform the functions ascribed to them herein. Memory 26 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 2:
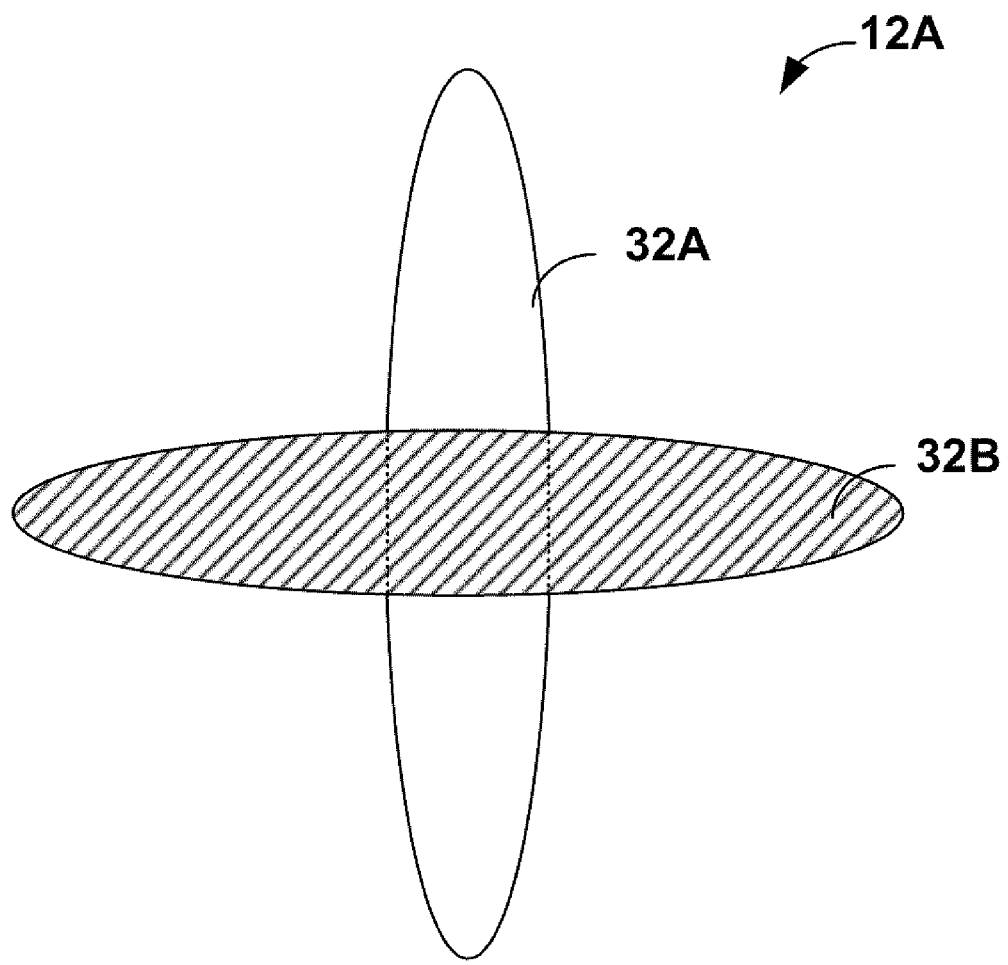
FIG. 2 is a conceptual diagram illustrating an example external antenna that may be used to locate an implanted object.

FIG. 2 is a conceptual diagram illustrating an example external antenna 12A that may be coupled to an external device 16 for location of an implanted object. As shown in FIG. 2, antenna includes a non-circular shape, which may increase the asymmetry of the loading of external antenna 12 when driven with different waveforms. More particularly, antenna 12A includes two oblong portions 32A and 32B (collectively "portions 32") that are arranged substantially similar to a cross, e.g., are arranged substantially perpendicularly and overlap approximately at their midpoints.

Portions 32 may be made of different materials with different loading profiles. Further, each of portions 32 may be driven with different waveforms. In this manner, the asymmetry of the loading of external antenna 12 when driven with different waveforms may be further increased.

Figure 3:
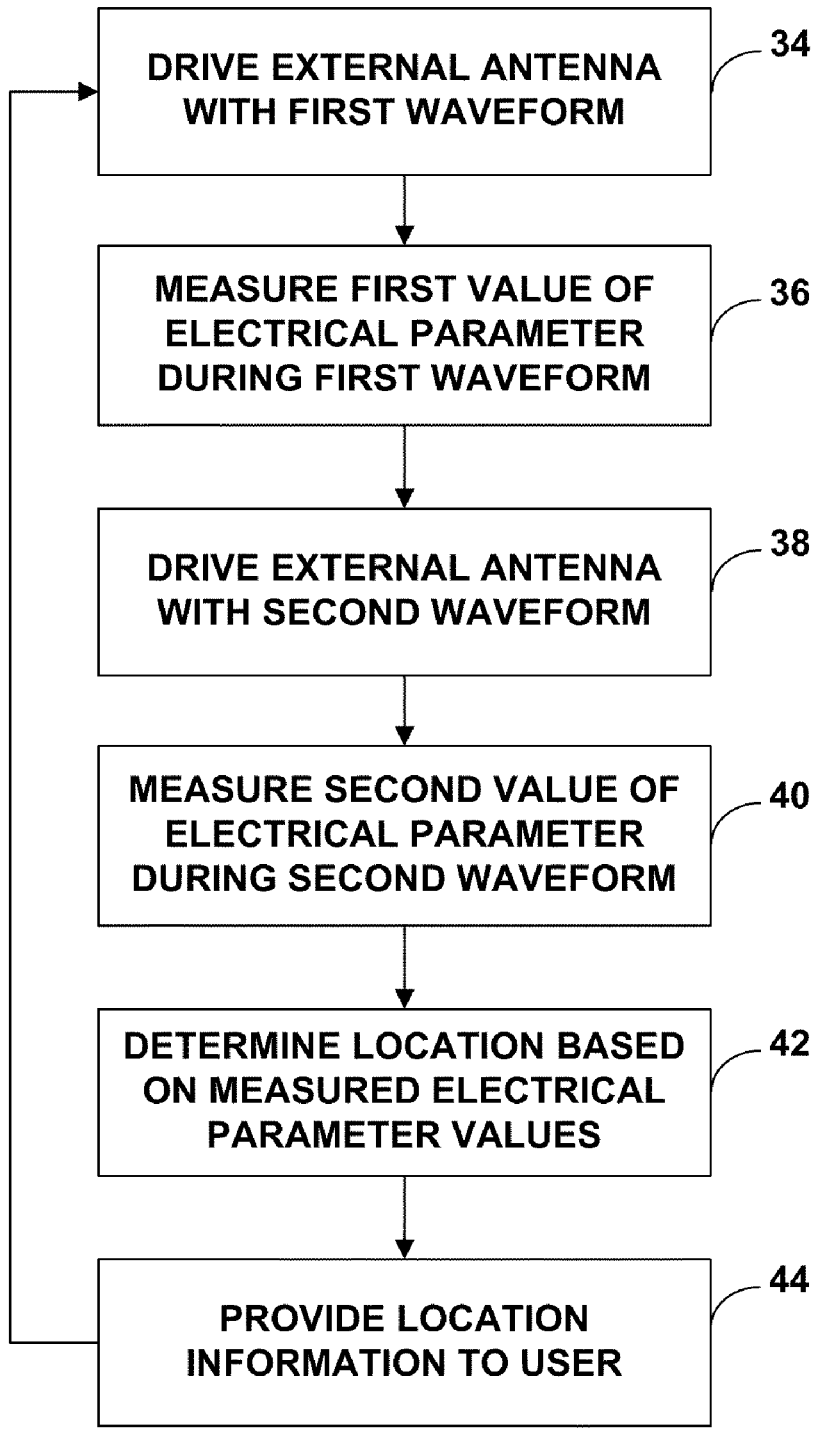
FIG. 3 is a flow diagram illustrating an example technique for locating an implanted object.

FIG. 3 is a flow diagram illustrating an example technique for locating an implanted object. According to the illustrated technique, external device 16 drives external antenna 12 with a first waveform (34). External device 16 measures a first value of an electrical parameter associated with external antenna 12 while the antenna is driven with the first waveform (36). External device 16 then drives external antenna 12 with a second waveform (38), and measures a second value of the electrical parameter (40).

External device 16 determines the location of an implanted object relative to external antenna 12 based on the first and second values of the electrical parameter (42). For example, external device 16 may apply equations that define position variables, such as radial distance (r) and depth (z) in terms of the electrical parameter, to the measured electrical parameter values, as described above. Based on the determined location, external device 16 provides location information to a physician or other user (44). For example, external device 16 may provide graphical, textual or audible indications of direction, distance, or the like, as described above.

Figure 4:
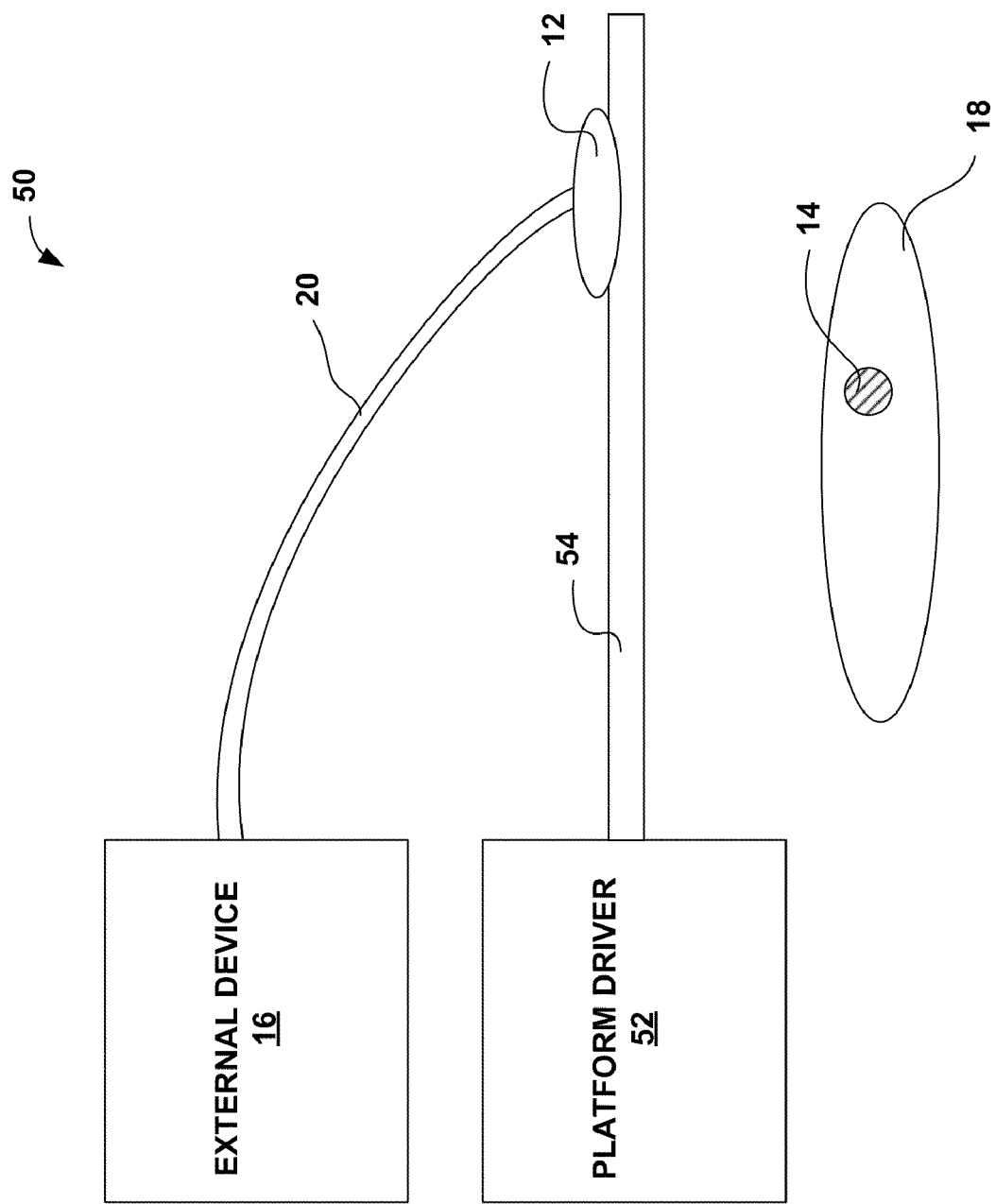
FIG. 4 is a block diagram illustrating an example system for determining position equations that may be used to determine the location of an implanted object based on measured values of an electrical parameter associated with an external antenna.

FIG. 4 is a block diagram illustrating an example system 50 for determining equations that may be used to determine the location of implanted object 14 based on measured values of an electrical parameter associated with external antenna 12, in the manner described above with reference to FIGS. 1 and 3. In the illustrated embodiment, system 50 includes external antenna 12, antenna 14, external device 16, IMD 18 and cable 20, described above with reference to FIG. 1. In other embodiments, system 50 may include a different external antenna, external device and cable. In other words, the external antenna, external device and cable used during determination of the equations need not be the same external antenna, external device and cable later used during application of the equations to locate the internal antenna.

The one or more equations used to determine the position of internal antenna 14 relative to external antenna 12 in the manner described above are determined prior to use of external device 16 and antenna 12 to locate antenna 14, when the location of antenna 14 is known. For example, the one or more equations may be determined prior to implantation of IMD 18 and antenna 14.

System 50 includes a platform driver 52, e.g., a robotic platform driver, that is capable of moving a platform 54 in a plurality of directions. In the illustrated embodiment, platform 54 supports antenna 12, and platform driver 52 moves platform 54 such that antenna 12 is moved through a three-dimensional region proximate to IMD 18 and antenna 14. The region may be above the IMD 18 and antenna 14, or may partially or completely surround the antenna. In other embodiments, platform 54 may support IMD 18 and antenna 14 instead of antenna 12, and platform driver moves platform such that IMD 18 and antenna 14 are moved through a three-dimensional region proximate to antenna.

While moving platform 54, platform driver 52 may determine the position the platform relative to an initial position. If antennas 12, 14 are aligned prior to movement of platform 54, the position of platform 54 may reflect the coordinate position (x,y,z) of antenna 12 relative to antenna 14. Platform driver 52 may periodically record such information when moving platform through the region proximate to IMD 18 and antenna 14. Platform driver 52 may include circuitry for communication with external device 16, and provide such information to the external device for determination of the equations.

While antenna 12 is moved through the three-dimensional region, external device 16 drives the external antenna with the two or more different waveforms, e.g., processor 22 (FIG. 1) controls generation of two or more waveforms to drive antenna 12. Processor 22 periodically measures values of an electrical parameter for each of the waveforms while antenna 12 is driven with the respective waveform.

Based on position information received from platform driver 52, processor 22 may determine the position of external antenna 12 relative to internal antenna 14 when each electrical parameter value was measured. Based on the measured electrical parameter values for each waveform, and the associated positions, processor 22 may determine a relationship between the position of external antenna 12 relative to internal antenna 14 and the electrical parameter for each of the waveforms. In other words, processor 22 may determine position/electrical parameter relationships for each waveform. Position/electrical parameter relationships may take the form of matrices.

Processor 22 may parametrically fit the position/electrical parameter relationships for each of the waveforms with equations of the form $ep=a+b*z+c*z^2+d*r$, where ep is the electrical parameter, e.g., current through the antenna or voltage across the antenna, z is the depth, r is the radial distance, and a, b, c and d are coefficients calculated using known z and r values. Platform driver 52 may record the values of r (radial distance) as antenna 12 is moved through the three-dimensional region, or the driver or external device may calculate radial distances at a later time based on recorded x and y values.

Processor 22 may solve the parametric equations for each of the position variables as a function of the electrical parameter. For example, processor 22 may solve the parametric equations for r and z in terms of the electrical parameter. In this manner, the processor may determine the plurality of equations, each equation relating a respective position variable to the electrical parameter.

Although described in terms of parametric equations, processor 22 may fit the position/electrical parameter relationships with equations of a higher order. For example, external device 16 drives external antenna 12 with additional waveforms, and determines additional position/electrical parameter relationships for each of the waveforms, higher order equations may be applied to the relationships to determine other position variables, such as angle ($\theta$), as described above.

As one example, processor 22 may control generation of first and second waveforms to drive external antenna 12 while it is moved first and second times through the region by platform driver 52. For each of the waveforms, processor 22 periodically measures the current through antenna 12 when the antenna is driven by the respective waveform. Processor 22 may measure currents at the same times during each movement of antenna 12 through the region, i.e., when antenna 12 is located at the same positions relative to antenna 14. Based on position information received from platform driver 52 and the measured currents, processor 22 determines position/current relationships for each of the waveforms. Processor 22 determines a parametric equation of best fit for each of the position/current relationships. For example, the parametric equations for the drive waveforms described above may be of the form:

$$i_{(1)}=a+b*z+c*z^2+d*r \qquad [6]$$

$$i_{(2)}=t+u*z+v*z^2+w*r \qquad [7]$$

where $i_{(1)}$ is current through antenna 12 when driven with the first waveform, $i_{(2)}$ is current through antenna 12 when driven with the first waveform, z is the depth, r is the radial distance, and a, b, c, d, t, u, v and w are coefficients calculated using known depths (z) and radial distances (r).

Next, processor 22 solves the parametric position equations for each of the position variables as a function of current measurement. For example, the equations may be solved for r and z in terms of current measurements. Below is an example in which the equations are solved for the variable z as a function of currents $i_{(i)}$ and $i_{(2)}$.

$$r = \frac{(i_{(1)} - a - b*z - c*z^2)}{d} \qquad [1] - \text{solve [6] for r}$$

$$[8] - \text{substitute [1] in [7]}$$

$$i_{(2)} = t + u*z + v*z^2 + \frac{w*i_{(1)}}{d} -$$
$$\frac{w*a}{d} - \frac{w*b*z}{d} - \frac{w*c*z^2}{d}$$

[9] – simplify [8]

$$0 = \left(v - \frac{w*c}{d}\right)z^2 +$$
$$\left(u - \frac{w*b}{d}\right)z + t - \frac{w*a}{d} + \frac{w*i_{(1)}}{d} - i_{(2)}$$

$$A = v - \frac{w*c}{d} \quad [3]$$

$$B = u - \frac{w*b}{d} \quad [4]$$

$$C = t - \frac{w*a}{d} + \frac{w*i_{(1)}}{d} - i_{(2)} \quad [5]$$

$$z = \frac{\left(-B \pm \sqrt{B^2 - 4*A*C}\right)}{2*A} \quad [2] - \text{quadratic equation}$$

Thus, processor 22 may determine depth (z) in by applying equation [2] to a measured current for each of the two waveforms. With z known, processor 22 may determine radial distance (r) by applying equation [1] to one of the measured currents. Equations [1] and [2] may be stored as position equations 30 in memory 26 of external device, as illustrated in FIG. 1, along with the values for a variety of constants. In embodiments, in which an external device different from the one used to determine equations 30 is later used to locate internal antenna, that external device may be programmed with information describing the waveforms 28 to be used and the equations.

In some embodiments, one or more other devices, rather than external device 16, perform some or all of the functions associated with determination of the equations. For example, platform driver 52 or another computing device may include a processor that determines the equations based on electrical parameter values received from external device, and programs the external device with the equations. Further, another device may perform some of the functions associated with the eventual location of the implanted object. For example, a separate computing device may receive measured electrical parameter values from external device 16 and include a processor that applies the equations to the measured values to determine the location of the implanted object relative to the antenna. The other device may also include a user interface to provide information to a user based on the determined location, in the manner described above with reference to external device 16.

Figure 5:
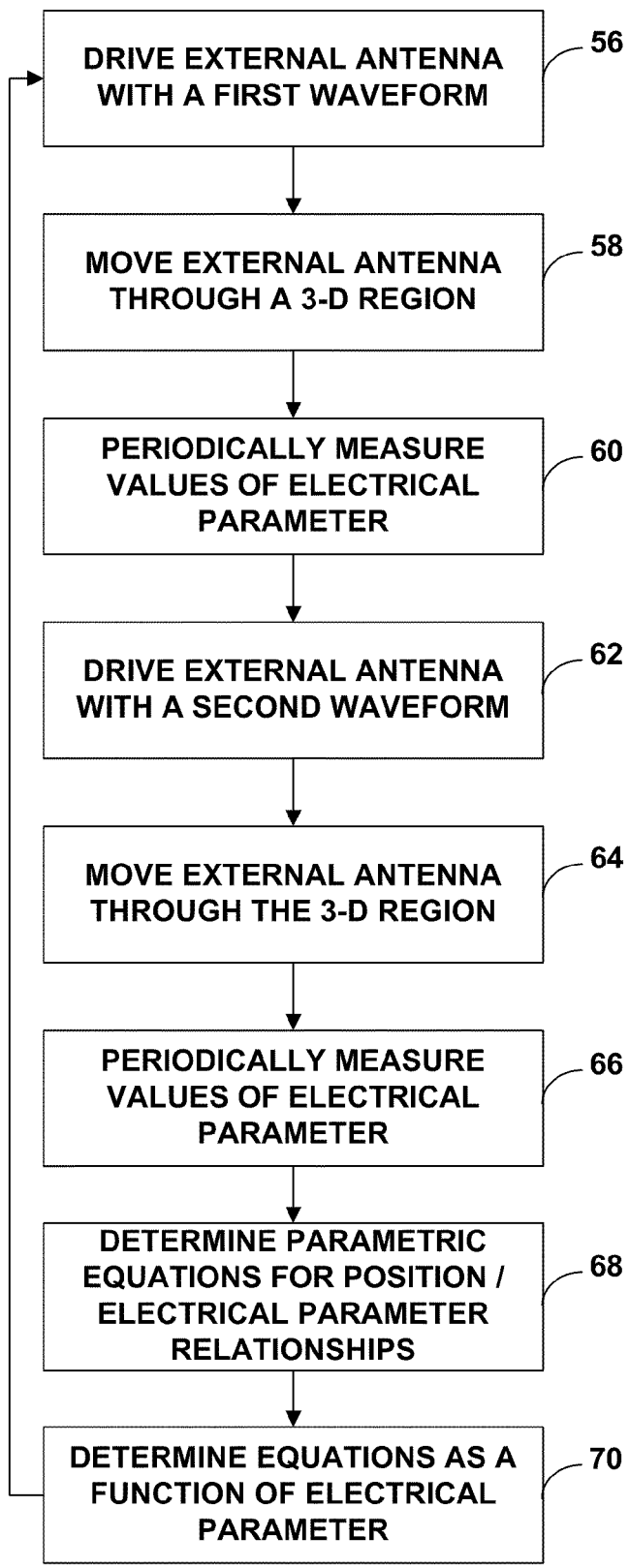
FIG. 5 is a flow diagram illustrating an example technique for determining position equations that may be used to determine the location of an implanted object based on measured values of an electrical parameter associated with an external antenna.

FIG. 5 is a flow diagram illustrating an exemplary initialization phase for determining equations that define the position of external antenna 12 relative to an internal object as a function of values of an electrical parameter. External device 16 drives external antenna 12 with a first waveform of a particular frequency, shape, pulse width and amplitude (56). External antenna 12 is moved through a three-dimensional proximate to the implanted object (58) a first time while the antenna is driven with the first waveform, and values of the electrical parameter are periodically measured while the antenna is driven with the first waveform (60).

External device 16 drives external antenna 12 with a second waveform has a different frequency, shape, amplitude, pulse width, or a combination thereof (62). External antenna 12 is moved through the region a second time while the antenna is driven with the second waveform (64). Values of the electrical parameter are periodically measured while external antenna 12 is moved though the region and driven with the second waveform (66).

Based on position information indicating the position of external antenna 12 relative to the implanted object when the current values were measured, external device 16 determines relationship between position (x,y,z) and current for each of the waveforms. From these relationships, external device 16 or a separate computing device determines parabolic equations that best fit each of the position/electrical parameter relationships (68). As described above, the equations may be of the form ep=a+b*z+c*$z^2$+d*r, where ep is the electrical parameter, e.g., current through the antenna or voltage across the antenna, z is the depth, r is the radial distance, and a, b, c and d are coefficients calculated using known z and r values. Using known current and position values, the values for the coefficients may be determined to define a parabolic equation that best fits the current/position relationships.

External device 16 or the separate computing device next determines position equations for z and r as a function of current measurements as described in detail above (70). The position equations may be stored in external device 16 as position equations 30 (FIG. 1). For example, the separate computing device may program the position equation into external device 16.

Figure 6A:
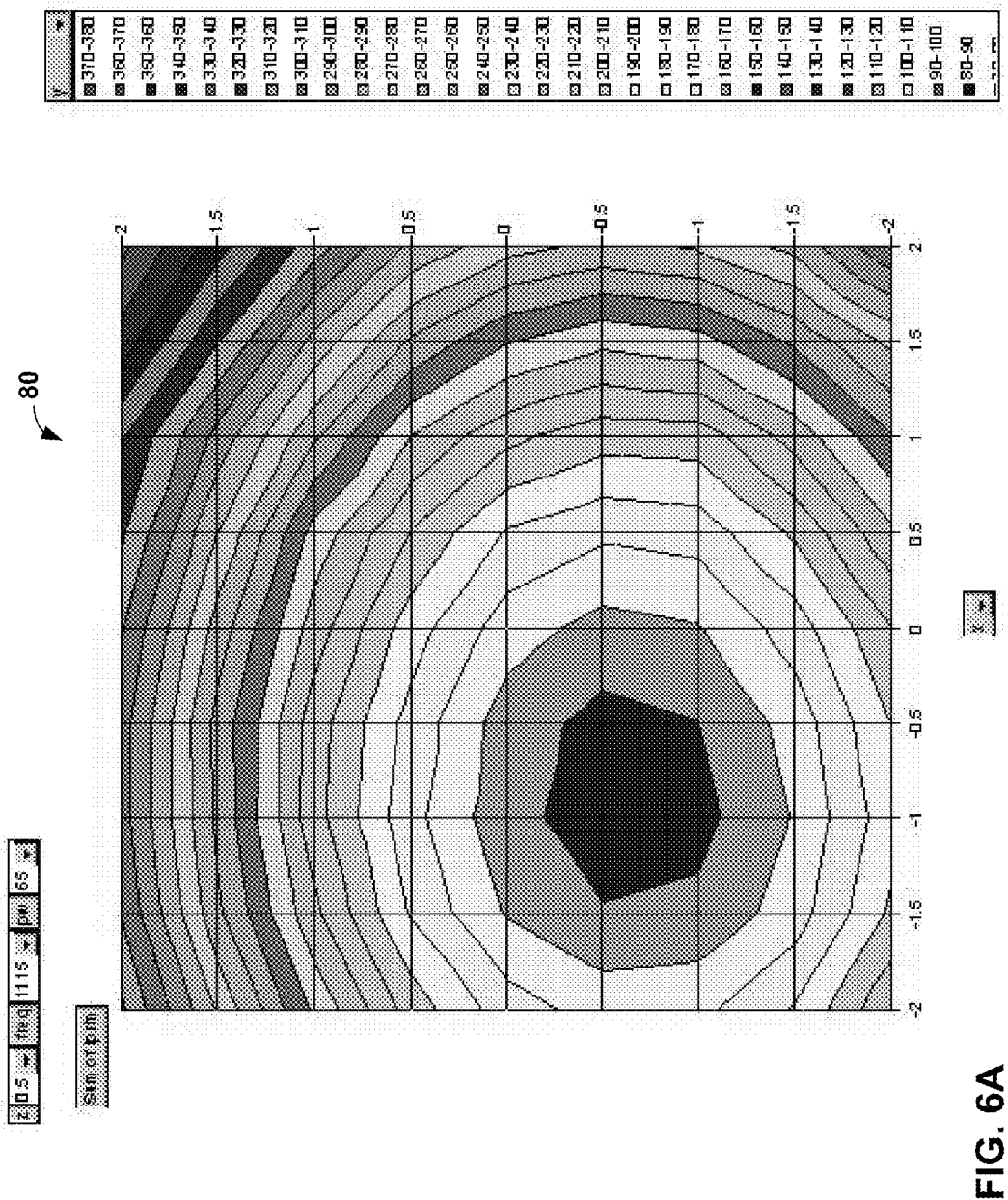
FIG. 6A and FIG. 6B are exemplary contour maps showing one planar slice of a three-dimensional relationship between position and current for respective drive waveforms.
Figure 6B:
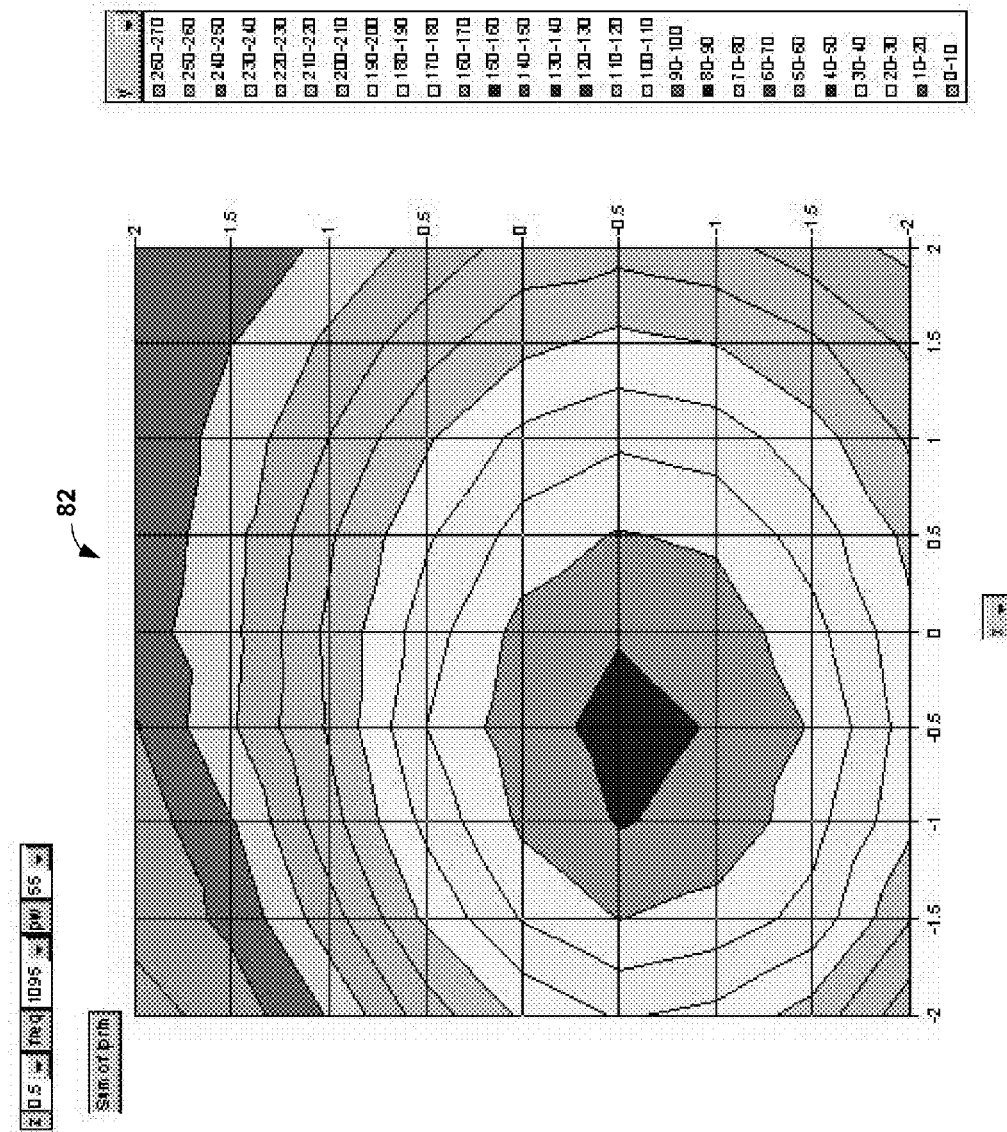

FIG. 6A and FIG. 6B are exemplary contour maps showing one planar slice (z=0.5) of the three-dimensional relationship between position and current for respective drive conditions. FIG. 6A illustrates a contour map 80 showing one planar slice of the three-dimensional relationship between position and current for a first drive condition, e.g., using a drive waveform with a frequency of 1115 Hz and an amplitude of 65 mV. FIG. 6B illustrates a contour map 82 showing one planar slice of the three-dimensional relationship between position and current for a second drive condition, e.g., using a drive waveform with a frequency of 1095 Hz and an amplitude of 55 mV. Contour maps 80, 82 illustrate asymmetric loading of antenna 12 when different waveforms are used to drive the antenna. Further, each of contour maps 80, 82 illustrates bands of constant current in relation to position. From such a relationship, one can get an idea of the distance from the center of the coil of external antenna 12 to the center of the implanted object.

Figure 7A:
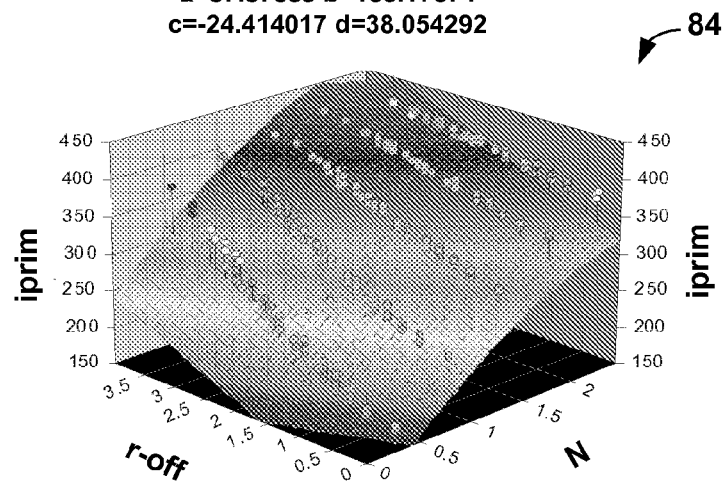
FIGS. 7A and 7B are exemplary diagrams illustrating fitting of current/position relationships with parametric equations.
Figure 7B:
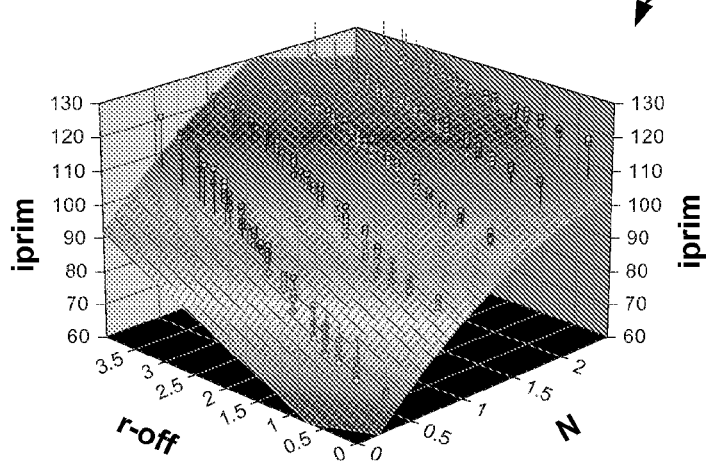

FIGS. 7A and 7B are exemplary diagrams illustrating the fitting of the current and position relationships with parametric equations. FIG. 7A illustrates a parametric equation fit 84 for the first measurement condition (i.e., drive waveform with a frequency of 1115 Hz and amplitude of 65 mV) and FIG. 7B illustrates a parametric equation fit 86 for the second measurement condition (i.e., drive waveform with a frequency of 1125 Hz and amplitude of 65 mV). FIGS. 7A and 7B indicate the form of the equation being used and identify the value of the constants calculated using the data points collected.

Various embodiments of the invention have been described. Although described primarily in the context of antenna alignment, the techniques of the invention may be used in any context in which location of an implanted object is desired. For example, the techniques may be used to locate a refill port of an implantable pump. These and other embodiments are within the scope of the following claims.

The invention claimed is:

1. A system comprising:
   an external antenna;
   an external device coupled to the external antenna that generates a first waveform, drives the external antenna with the first waveform while the external antenna is moved through a three-dimensional region proximate to an implantable object a first time, periodically measures values of an electrical parameter associated with the external antenna while the external antenna is moved through the three-dimensional region the first time and driven with the first waveform, generates a second waveform that has at least one different waveform parameter than the first waveform, drives the external antenna with the second waveform while the external antenna is moved through the three-dimensional region a second time, and periodically measures values of the electrical parameter while the external antenna is moved through the three-dimensional region the second time and driven with the second waveform; and a processor that determines a first position/electrical parameter relationship based on the electrical parameter values measured while the external antenna was driven with the first waveform and positions within the three-dimensional region at which the external antenna was located when the electrical parameter values were measured, determines a second position/electrical parameter relationship based on the electrical parameter values measured while the external antenna was driven with the second waveform and positions within the three-dimensional region at which the external antenna was located when the electrical parameter values were measured, and determines first and second equations based on the first and second position/electrical parameter relationships, wherein the first equation defines a first position variable as a function of the electrical parameter and the second equation defines a second position variable as a function of the electrical parameter.

2. The system of claim 1, wherein the first position variable comprises a radial distance, and the second position variable comprises a depth.

3. The system of claim 1,
wherein the external device generates a third waveform that has at least one different waveform parameter than the first and second waveforms, drives the external antenna with the third waveform while the external antenna is moved through the three-dimensional region a third time, and periodically measures values of the electrical parameter while the external antenna is moved through the three-dimensional region the third time and driven with the third waveform, wherein the processor determines a third position/electrical parameter relationship based on the electrical parameter values measured while the external antenna is driven with the third waveform and positions within the three-dimensional region at which the external antenna was located when the electrical parameter values were measured, and determines the first and second equations based on the first, second and third position/electrical parameter relationships, and wherein the first position variable comprises a radial distance, and the second position variable comprises an angle.

4. The system of claim 1, wherein the processor determines the first and second equations by fitting a parametric equation to each of the position/electrical parameter relationships.

5. The system of claim 1, wherein the external antenna is moved through the three-dimensional region proximate to the object prior to implantation of the object.

6. The system of claim 1, wherein the processor comprises a processor of the external device.

7. The system of claim 1, wherein the processor stores information identifying the first and second waveforms and the first and second determined equations in a memory of the external device or of another external device for determination of a location of the object relative the external antenna when the object is implanted.

8. The system of claim 1, wherein the first and second waveforms are predetermined waveforms.

9. A non-transitory computer-readable medium comprising instructions that cause a programmable processor to:
control generation of a first waveform in an external device to drive an external antenna while the external antenna is moved through a three-dimensional region proximate to an implantable object a first time;

periodically measure values of an electrical parameter associated with the external antenna while the external antenna is moved through the three-dimensional region the first time and driven with the first waveform;

determine a first position/electrical parameter relationship based on the electrical parameter values measured while the external antenna was driven with the first waveform and positions within the three-dimensional region at which the external antenna was located when the electrical parameter values were measured;

control generation of a second waveform in the external device to drive the external antenna while the external antenna is moved through the three-dimensional region a second time, wherein the second waveform has at least one different waveform parameter than the first waveform;

periodically measure values of the electrical parameter while the external antenna is moved through the three-dimensional region the second time and driven with the second waveform;

determine a second position/electrical parameter relationship based on the electrical parameter values measured while the external antenna was driven with the second waveform and positions within the three-dimensional region at which the external antenna was located when the electrical parameter values were measured; and determine first and second equations based on the first and second position/electrical parameter relationships, wherein the first equation defines a first position variable as a function of the electrical parameter, and the second equation defines a second position variable as a function of the electrical parameter.

10. The computer-readable medium of claim 9, wherein the instructions that cause a programmable processor to determine first and second equations comprise instructions that cause a programmable processor to fit a parametric equation to each of the position/electrical parameter relationships.

11. The computer-readable medium of claim 9, further comprising instructions that cause a programmable processor to store information identifying the first and second waveforms and the first and second determined equations in a memory of an external device that one of programs, recharges, or refills an implantable medical device associated with the implantable object.

12. The computer-readable medium of claim 9, wherein the instructions that cause the programmable processor to control the generation of the first and second waveforms comprise instructions that cause the programmable processor to control the generation of first and second predetermined waveforms.

* * * * *